United States Patent
Wang et al.

(10) Patent No.: US 8,695,401 B2
(45) Date of Patent: *Apr. 15, 2014

(54) HANDHELD GAS ANALYSIS SYSTEMS FOR POINT-OF-CARE MEDICAL APPLICATIONS

(75) Inventors: Li-Peng Wang, San Jose, CA (US); Chien-Lin Huang, Shinjhuang (TW); Tsung-Kuan A. Chou, San Jose, CA (US)

(73) Assignee: TricornTech Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/332,064

(22) Filed: Dec. 20, 2011

(65) Prior Publication Data
US 2012/0090378 A1 Apr. 19, 2012

Related U.S. Application Data

(63) Continuation of application No. 12/140,822, filed on Jun. 17, 2008, now Pat. No. 8,087,283.

(51) Int. Cl.
*G01N 30/02* (2006.01)
(52) U.S. Cl.
USPC ............ 73/23.4; 73/23.35; 73/23.41; 96/101; 422/89
(58) Field of Classification Search
USPC ............ 73/23.35, 23.4, 23.41, 23.42; 96/101; 422/89
See application file for complete search history.

(56) References Cited

U.S. PATENT DOCUMENTS

| | | | |
|---|---|---|---|
| 4,470,298 A | 9/1984 | Jibelian | |
| 4,869,876 A | 9/1989 | Arfman et al. | |
| 4,888,295 A | 12/1989 | Zaromb et al. | |
| 5,092,155 A | * 3/1992 | Rounbehler et al. | 73/23.41 |
| 5,108,468 A | 4/1992 | Ligon, Jr. | |
| 5,108,705 A | * 4/1992 | Rounbehler et al. | 422/89 |
| 5,109,691 A | 5/1992 | Corrigan et al. | |
| 5,611,846 A | 3/1997 | Overton et al. | |

(Continued)

FOREIGN PATENT DOCUMENTS

| | | |
|---|---|---|
| CN | 1979172 A | 6/2007 |
| CN | 101196457 A | 6/2008 |

(Continued)

OTHER PUBLICATIONS

EP Application No. 09767436.0, Supplementary European Search Report and the European Search Opinion, Dec. 22, 2011, 8 pages.

(Continued)

*Primary Examiner* — Daniel S Larkin
(74) *Attorney, Agent, or Firm* — Blakely Sokoloff Taylor & Zafman LLP

(57) ABSTRACT

The disclosure describes a substrate with a fluid-handling assembly coupled to the substrate, the fluid-handling assembly including a plurality of fluid-handling components removably coupled to the substrate and removably coupled to each other. The plurality of fluid handling components includes a gas chromatograph having a fluid inlet and a fluid outlet, and a detector array having a fluid inlet and a fluid outlet, wherein the fluid inlet of the detector array is fluidly coupled to the fluid outlet of the gas chromatograph. A control circuit is communicatively coupled to at least one of the plurality of fluid-handling components, and a readout circuit communicatively coupled to the detector array and to the control circuit. Other embodiments are disclosed and claimed.

28 Claims, 8 Drawing Sheets

(56) References Cited

U.S. PATENT DOCUMENTS

| | | | |
|---|---|---|---|
| 6,306,200 | B1 | 10/2001 | Yu |
| 6,497,138 | B1 | 12/2002 | Abdel-Rahman et al. |
| 6,828,910 | B2 | 12/2004 | VanRyzin et al. |
| 6,914,220 | B2 | 7/2005 | Tian et al. |
| 7,153,272 | B2 | 12/2006 | Talton |
| 7,343,779 | B1 | 3/2008 | Yu |
| 7,926,368 | B2 | 4/2011 | Ryan |
| 8,087,283 | B2 | 1/2012 | Wang et al. |
| 2003/0015019 | A1 | 1/2003 | O'Brien |
| 2003/0233862 | A1 | 12/2003 | Wise et al. |
| 2004/0236244 | A1 | 11/2004 | Allen et al. |
| 2005/0063865 | A1 | 3/2005 | Bonne et al. |
| 2005/0065446 | A1 | 3/2005 | Talton |
| 2005/0085740 | A1 | 4/2005 | Davis et al. |
| 2006/0046749 | A1 | 3/2006 | Pomerantz et al. |
| 2006/0222568 | A1 | 10/2006 | Wang et al. |
| 2007/0000305 | A1 | 1/2007 | Ma et al. |
| 2007/0000838 | A1 | 1/2007 | Shih et al. |
| 2007/0062255 | A1 | 3/2007 | Talton |
| 2007/0256474 | A1 | 11/2007 | Paakkanen et al. |
| 2008/0092626 | A1 | 4/2008 | Lehmann |
| 2008/0121016 | A1* | 5/2008 | Shah et al. .................. 73/23.42 |
| 2008/0233636 | A1 | 9/2008 | Ryan |
| 2008/0264491 | A1 | 10/2008 | Klee et al. |
| 2008/0300501 | A1 | 12/2008 | Willard et al. |
| 2009/0308136 | A1 | 12/2009 | Wang et al. |
| 2011/0005300 | A1 | 1/2011 | Wang et al. |
| 2011/0023581 | A1 | 2/2011 | Chou et al. |
| 2011/0259081 | A1 | 10/2011 | Chou et al. |

FOREIGN PATENT DOCUMENTS

| | | | |
|---|---|---|---|
| DE | 196 01 571 A1 | 7/1997 | |
| EP | 0 573 060 A2 | 12/1993 | |
| EP | 0 574 027 A2 | 12/1993 | |
| EP | 0 654 667 A1 | 5/1995 | |
| EP | 2 065 704 A1 | 6/2009 | |
| GB | 874 742 A | 8/1961 | |
| JP | 06 242095 A | 9/1994 | |
| JP | 07 318545 A | 12/1995 | |
| JP | 2009-183905 | 8/2009 | |
| WO | WO 2009/057256 A1 | 5/2009 | |

OTHER PUBLICATIONS

PCT/US2011/033325, International Search Report and Written Opinion of the International Searching Authority, mail date Jan. 6, 2012, 7 pages.
Manolis, A., "The Diagnostic Potential of Breath Analysis," Clinical Chemistry, vol. 29, No. 1, pp. 5-15, (1983).
Ho, C. K. et al., "Review of Chemical Sensors for In-Situ Monitoring of Volatile Contaminants," Sandia Report, SAND2001-0643, pp. 1-28, (2001).
Riegel, J. et al., "Exhaust gas sensors for automotive emission control," Solid State Ionics 152-153, pp. 783-800, (2002).
Eranna, G. et al., "Oxide Materials for Development of Integrated Gas Sensors—A Comprehensive Review," Critical Reviews in Solid State and Materials Sciences, 29, pp. 111-188, (2004).
Arshak, K. et al., "A review of gas sensors employed in electronic nose applications," Sensor Review, vol. 24, No. 2, pp. 181-198, (2004).
Yamazoe, N., "Toward innovations of gas sensor technology,", Sensors and Actuators B 108, pp. 2-14, (2005).
Cao, W. et al., "Breath Analysis: Potential for Clinical Diagnosis and Exposure Assessment," Clinical Chemistry 52, No. 5, pp. 800-811, (2006).
Buszewski, B. et al., "Human exhaled air analytics: biomarkers of diseases" Biomedical Chromatography, 21, pp. 553-566, (2007).
Ohira, S.-I. et al., "Micro gas analyzers for environmental and medical applications," Analytica Chimica Acta 619, pp. 143-156, (2008).
Peng, G. et al., "Diagnosing lung cancer in exhaled breath using gold nanoparticles," Nature Nanotechnology, vol. 4, pp. 669-673, (2009).

Barnes, P. J. et al., "Exhaled Nitric Oxide in Pulmonary Diseases: A Comprehensive Review," Chest, 138/3, pp. 682-692, (2010).
Rollins, G., "Beyond Breathalyzers: What Clinical Niche Will Breath Tests Fill?" Clinical Laboratory News, vol. 37, No. 5, pp. 1-6, (2011).
Wohltjen, H. et al., "Colloidal Metal-Insulator-Metal Ensemble Chemiresistor Sensor," Analytical Chemistry, vol. 70, No. 14, Jul. 15, 1998, pp. 2856-2859.
Dutta, R. et. al., "Bacteria Classification using Cyranose 320 Electronic Nose," BioMedical Engineering OnLine 2002, Oct. 16, 2002, 7 pages.
de Alencastro, L. F. et al., "Application of Multidimensional (Heart-Cut) Gas Chromatography to the Analysis of Complex Mixtures of Organic Pollutants in Environmental Samples," Environmental Analysis, Chimia 57, No. 9, (2003) pp. 499-504.
Lambertus, G. et. al., "Design, Fabrication, and Evaluation of Microfabricated Columns for Gas Chromatography," Analytical Chemistry, vol. 76, No. 9, May 1, 2004, pp. 2629-2637.
Hanson III, C.W. et al., "Electronic Nose Prediction of a Clinical Pneumonia Score: Biosensors and Microbes," Anesthesiology, V 102, No. 1, Jan. 2005, pp. 63-68.
Lambertus, G. et al., "Stop-Flow Programmable Selectivity with a Dual-Column Ensemble of Microfabricated Etched Silicon Columns and Air as Carrier Gas," Analytical Chemistry, vol. 77, No. 7, Apr. 1, 2005, pp. 2078-2084.
Tian, W. et al., "Multiple-Stage Microfabricated Preconcentrator-Focuser for Micro Gas Chromatography System," Journal of Microelectromechanical Systems, vol. 14, No. 3, Jun. 2005, pp. 498-507.
Libardoni, M. et al., "Analysis of human breath samples with a multi-bed sorption trap and comprehensive two-dimensional gas chromatography (GC×GC)," Journal of Chromatography B, 842, (2006), pp. 13-21.
Phillips, M. et. al., "Prediction of lung cancer using volatile biomarkers in breath[1]," Cancer Biomarkers, 3, (2007), pp. 95-109.
Rowe, M.P. et. al., "Exploiting Charge-Transfer Complexation for Selective Measurement of Gas-Phase Olefins with Nanoparticle-Coated Chemiresistors," Analytical Chemistry, vol. 79, No. 3, Feb. 1, 2007, pp. 1164-1172.
Bae, B. et al., "A Fully-Integrated MEMS Preconcentrator for Rapid Gas Sampling," Transducers & Eurosensors'07, The 14th International Conference on Solid-State Sensors, Actuators and Microsystems, Lyon, France, Jun. 10-14, 2007, 2007 IEEE, pp. 1497-1500.
Phillips, M. et. al., "Volatile biomarkers of pulmonary tuberculosis in the breath," Tuberculosis, (2007) 87, pp. 44-52.
Phillips, M. et al., "Breath biomarkers of active pulmonary tuberculosis," Tuberculosis (2010) pp. 1-7.
PCT/US2009/045872, International Search Report and Written Opinion of the International Searching Authority, mail date Jul. 27, 2009, 11 pages.
PCT/US2010/041243, International Search Report and Written Opinion of the International Searching Authority, mail date Feb. 17, 2011, 7 pages.
PCT/US2010/044165, International Search Report and Written Opinion of the International Searching Authority, mail date Apr. 29, 2011, 8 pages.
U.S. Office Action mailed Dec. 22, 2010, U.S. Appl. No. 12/140,822, filed Jun. 17, 2008, 16 pages.
U.S. Office Action mailed May 18, 2011, U.S. Appl. No. 12/140,822, filed Jun. 17, 2008, 6 pages.
U.S. Notice of Allowance mailed Aug. 30, 2011, U.S. Appl. No. 12/140,822, filed Jun. 17, 2008, 9 pages.
A. Hansel et al., "Proton transfer reaction mass spectrometry: on-line trace gas analysis at the ppb level," International Journal of Mass Spectrometry and Ion Processes, vols. 149-150, Nov. 15, 1995, pp. 609-619.
Auble, D.L. et al., "An open path, fast response infrared absorption gas analyzer for H2O and CO2," Boundary-Layer Meteorology, 1992, vol. 59, pp. 243-256.
Y. Aimin et al., "Analysis of Gas by a Portable Gas Chromatograph With a Microwave Induced Plasma Ionization Detector," Chinese Journal of Analytical Chemistry, 1993, vol. 21, No. 6, pp. 736-739.

(56) References Cited

OTHER PUBLICATIONS

Y. Haiying et al., "A New GC System for the Analysis of Permanent Gases," Rock and Mineral Analysis, Mar. 1999, vol. 18, No. 1, pp. 29-33, Beijing, China.

B. Shi, "Application of 4 200 Ultra-fast GC Analyzer to Environment Emergence Monitoring," Liaoning Urban and Rural Environmental Science & Technology, 2006, vol. 26, No. 6, pp. 34-35.

CN 200980123127.X—First Chinese Office Action, mailed Feb. 1, 2013, 27 pages.

U.S. Appl. No. 12/830,682—Non-Final Office Action, mailed Sep. 4, 2012, 21 pages.

U.S. Appl. No. 12/847,593—Non-Final Office Action, mailed Dec. 20, 2012, 6 pages.

Tian, W. et al., "Microfabricated Preconcentrator-Focuser for a Microscale Gas Chromatograph," Journal of Microelectromechanical Systems, vol. 12, No. 3, Jun. 2003, pp. 264-272.

U.S. Appl. No. 12/830,682—Final Office Action, mailed Apr. 29, 2013, 22 pages.

U.S. Appl. No. 12/847,593—Final Office Action, mailed Jul. 18, 2013, 8 pages.

CN 2010-80031094.9—First Chinese Office Action, mailed Sep. 12, 2013, 15 pages.

CN 2009-80123127.X—Second Chinese Office Action, mailed Sep. 24, 2013, 13 pages.

EP 10 79 7800—EPO Supplementary European Search Report and European Search Opinion, dated Sep. 25, 2013, 6 pages.

\* cited by examiner

HANDHELD GAS ANALYSIS SYSTEMS FOR POINT-OF-CARE MEDICAL APPLICATIONS

CROSS-REFERENCE TO RELATED APPLICATIONS

This application is a continuation of U.S. patent application Ser. No. 12/140,822, filed 17 Jun. 2008, and claims priority therefrom under 35 U.S.C. §120. The priority application is now U.S. Pat. No. 8,087,283.

TECHNICAL FIELD

The present invention relates generally to gas analysis systems and in particular, but not exclusively, to handheld gas analysis systems for point-of-care medical applications.

BACKGROUND

Gas analysis can be an important means for detecting the presence and concentration of certain chemicals in the gas and determining the meaning of the particular combination of chemicals present. In health care, for example, the presence of certain volatile organic compounds (VOCs) in exhaled human breath are correlated to certain diseases, such as pneumonia, pulmonary tuberculosis (TB), asthma, lung cancer, liver diseases, kidney diseases, etc. The correlations are especially evidential for lung-related diseases. In other applications, gas analysis can be used to determine the presence of dangerous substances incompatible with human presence, such as methane, carbon monoxide or carbon dioxide in a mine.

Current gas analytical systems still rely heavily on large and expensive laboratory instruments, such as gas chromatography (GC) and mass spectrometry (MS). Most of these instruments (mass spectrometers in particular) have operational characteristics that prevent significant reductions in their size, meaning that current gas analysis systems are large and expensive bench devices. In addition to being expensive and unwieldy, the large size of current gas analysis devices makes widespread use of these instruments impossible.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION OF THE ILLUSTRATED EMBODIMENTS

Embodiments of an apparatus, process and system for gas analysis in point-of-care medical applications are described herein. In the following description, numerous specific details are described to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail but are nonetheless encompassed within the scope of the invention.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in this specification do not necessarily all refer to the same embodiment. Furthermore, the particular features, structures, or characteristics may be combined in any suitable manner in one or more embodiments.

Figure 1A:
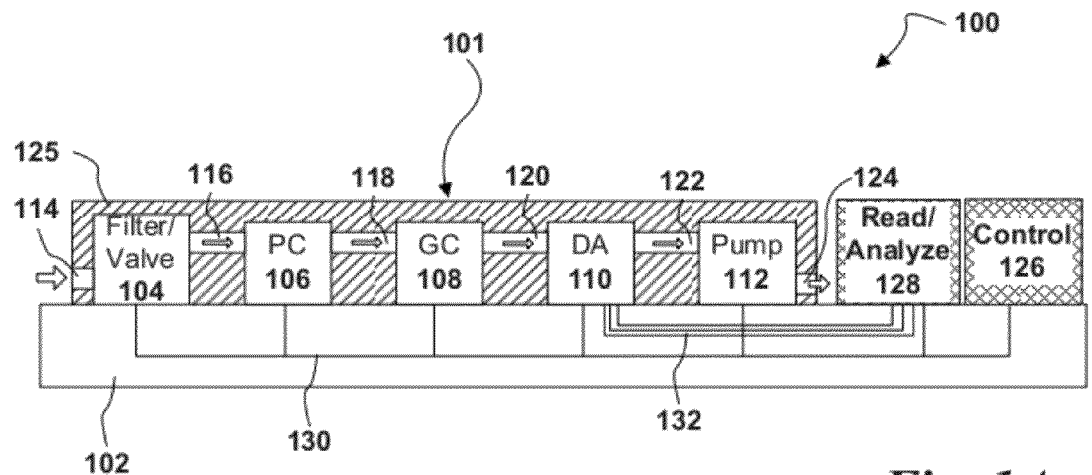
FIG. 1A is a side elevation drawing of an embodiment of a gas analysis device.
Figure 1B:
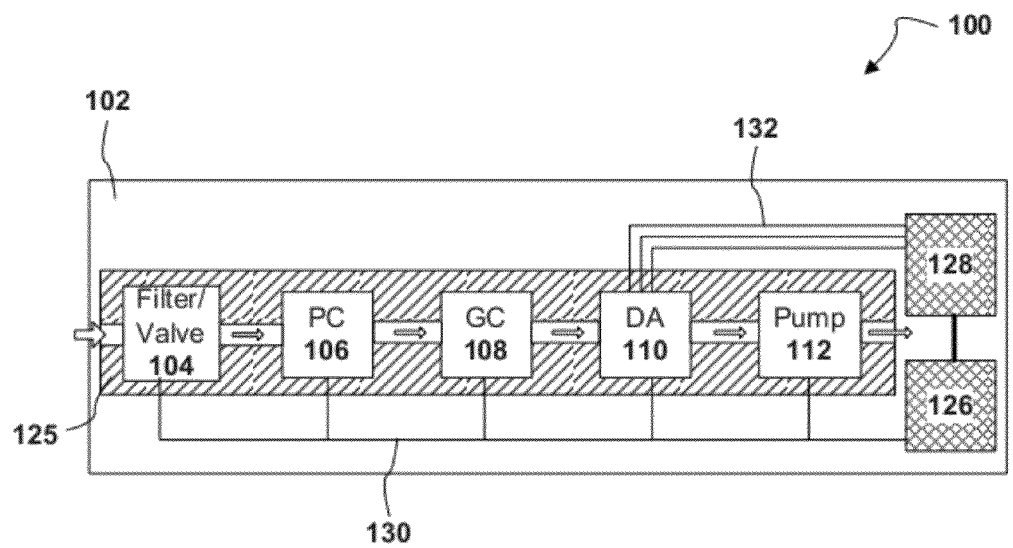
FIG. 1B is a plan view of the embodiment of a gas analysis device shown in FIG. 1.

FIGS. 1A and 1B together illustrate an embodiment of a small scale (e.g., handheld) gas analysis device 100. Device 100 includes a substrate 102 on which are mounted a fluid handling assembly 101, a controller 126 coupled to the individual elements within fluid handling assembly 101, and a reading and analysis circuit 128 coupled to detector array 110 and to controller 126. The embodiment shown in the figures illustrates one possible arrangement of the elements on substrate 102, but in other embodiments the elements can, of course, be arranged on the substrate differently.

Substrate 102 can be any kind of substrate that provides the required physical support and communication connections for the elements of device 100. In one embodiment, substrate 102 can be a printed circuit board (PCB) of the single-layer variety with conductive traces on its surface, but in other embodiments it can be a PCB of the multi-layer variety with conductive traces in the interior of the circuit board. In other embodiments, for example an embodiment where device 100 is built as a monolithic system on a single die, substrate 102 can be chip or wafer made of silicon or some other semiconductor. In still other embodiments, substrate 102 can also be a chip or wafer in which optical waveguides can be formed to support optical communication between the components of device 100.

Fluid handling assembly 101 includes a filter and valve assembly 104, a pre-concentrator 106, a gas chromatograph 108, a detector array 110 and a pump 112. Elements 104-112 are fluidly coupled in series: filter and valve assembly 104 is fluidly coupled to pre-concentrator 106 by fluid connection 116, pre-concentrator 106 is fluidly coupled to gas chromatograph 108 by fluid connection 118, gas chromatograph 108 is fluidly coupled to detector array 110 by fluid connection 120, and detector array 110 is coupled to pump 112 by fluid connection 122. As further described below, in one embodiment of device 100 elements 104-112 can be micro-electro-mechanical (MEMS) elements or MEMS-based elements, meaning that some parts of each device can be MEMS and other parts not. In other embodiments of device 100, some or all of elements 104-112 need not be MEMS or MEMS-based, but can instead be some non-MEMS chip scale device.

As indicated by the arrows in the figures, the fluid connections between elements 104-112 allow a fluid (e.g., one or more gases) to enter filter and valve assembly 104 through inlet 114, flow though elements 104-112, and finally exit pump 112 through outlet 124. Fluid handling assembly 101 also includes a shroud or cover 125 that protects individual elements 104-112. In the illustrated embodiment, channels formed in shroud 125 provide the fluid connections between the elements, but in other embodiments the fluid connections between elements can be provided by other means, such as tubing. In still other embodiments shroud 125 can be omitted.

Filter and valve assembly 104 includes an inlet 114 and an outlet coupled to fluid connection 116 such that fluid exiting filter and valve assembly 104 flows into pre-concentrator 110. Filter and valve assembly 104 includes a filter to remove particulates from fluid entering through inlet 114. In embodiments of device 100 where one or more of elements 104-112 is a MEMS element, the small scale of parts within the MEMS elements of device pre-concentrator means that fluid entering through inlet 114 can be filtered to remove these particles so that the particles do not enter the MEMS devices and either damage them or render them inoperative. In embodiments of device 100 that include no MEMS components or where fluid entering inlet 114 contains no particles, for instance because it has been pre-filtered externally to device 100, the filter portion of filter and valve assembly 104 can be omitted.

Filter and valve assembly 104 also includes a valve so that further flow through inlet 114 into fluid handling assembly 101 can be stopped once sufficient fluid has passed through the device. Stopping further flow through inlet 114 prevents dilution of fluids that will flow out of pre-concentrator 106 during later operation of device 100 (see description of operation below). In other embodiments, filter and valve assembly 104 can also include a de-humidifier to remove water vapor from the fluid entering through inlet 114, thus improving the accuracy and sensitivity of device 100.

Pre-concentrator 106 includes an inlet coupled to fluid connection 116 and an outlet coupled to fluid connection 118. Pre-concentrator 106 receives fluid from filter and valve assembly 104 through fluid connection 116 and outputs fluid to gas chromatograph 108 through fluid connection 118. As fluid flows through pre-concentrator 106, the pre-concentrator absorbs certain chemicals from the passing fluid, thus concentrating those chemicals for later separation and detection. In one embodiment of device 100 pre-concentrator 106 can be a MEMS pre-concentrator, but in other embodiments pre-concentrator 106 can be a non-MEMS chip scale device. Further details of an embodiment of a MEMS pre-concentrator are described below in connection with FIG. 2.

Gas chromatograph 108 includes an inlet coupled to fluid connection 118 and an outlet coupled to fluid connection 120. Gas chromatograph 108 receives fluid from pre-concentrator 106 through fluid connection 118 and outputs fluid to detector array 110 through fluid connection 120. As fluid received from pre-concentrator 106 flows through gas chromatograph 108, individual chemicals in the fluid received from the pre-concentrator are separated from each other in the time domain for later input into detector array 110. In one embodiment of device 100 gas chromatograph 108 can be a MEMS gas chromatograph, but in other embodiments gas chromatograph 108 can be a non-MEMS chip scale device. Further details of an embodiment of a MEMS gas chromatograph 108 are described below in connection with FIGS. 3A-3B.

Detector array 110 includes an inlet coupled to fluid connection 120 and an outlet coupled fluid connection 122. Detector array 110 receives fluid from gas chromatograph 108 through fluid connection 120 and outputs fluid to pump 112 through fluid connection 122. As fluid flows through detector array 110, the chemicals that were time-domain separated by gas chromatograph 108 enter the detector array and their presence and/or concentration is sensed by sensors within the detector array. In one embodiment of device 100 detector array 110 can be a MEMS detector array, but in other embodiments detector array 110 can be a non-MEMS chip scale device. Further details of an embodiment of a detector array 110 are described below in connection with FIG. 4.

Pump 112 includes an inlet coupled to fluid connection 122, as well as an outlet coupled to an exhaust 124, such that pump 112 draws fluid from detector array 110 through fluid connections 122 and returns it to the atmosphere through exhaust 124. Pump 112 can be any kind of pump that meets the size and form factor requirements of device 100, provides the desired flow rate and flow rate control, and has adequate reliability (i.e., an adequate mean time between failures (MTBF)). In one embodiment, pump 112 can be a MEMS or MEMS-based pump, but in other embodiments it can be another type of pump. Examples of pumps that can be used include small axial pumps (e.g., fans), piston pumps, and electro-osmotic pumps.

Controller 126 is communicatively coupled to the individual elements within fluid handling assembly 101 such that it can send control signals and/or receive feedback signals from the individual elements. In one embodiment, controller 126 can be an application-specific integrated circuit (ASIC) designed specifically for the task, for example a CMOS controller including processing, volatile and/or non-volatile storage, memory and communication circuits, as well as associated logic to control the various circuits and communicate externally to the elements of fluid handling assembly 101. In other embodiments, however, controller 126 can instead be a general-purpose microprocessor in which the control functions are implemented in software. In the illustrated embodiment controller 126 is electrically coupled to the individual elements within fluid handling assembly 101 by conductive traces 130 on the surface or in the interior of substrate 102, but in other embodiments controller 126 can be coupled to the elements by other means, such as optical.

Readout and analysis circuit 128 is coupled to an output of detector array 110 such that it can receive data signals from individual sensors within detector array 110 and process and analyze these data signals. In one embodiment, readout and analysis circuit 128 can be an application-specific integrated circuit (ASIC) designed specifically for the task, such as a CMOS controller including processing, volatile and/or non-volatile storage, memory and communication circuits, as well as associated logic to control the various circuits and communicate externally. In other embodiments, however, readout and analysis circuit 128 can instead be a general-purpose microprocessor in which the control functions are implemented in software. In some embodiments readout and analysis circuit 128 can also include signal conditioning and processing elements such as amplifiers, filters, analog-to-digital converters, etc., for both pre-processing of data signals received from detector array 110 and post-processing of data generated or extracted from the received data by readout and analysis circuit 128.

In the illustrated embodiment, readout and analysis circuit 128 is electrically coupled to detector array 110 by conductive traces 132 positioned on the surface or in the interior of substrate 102, but in other embodiments controller 126 can be coupled to the elements by other means, such as optical means. Readout and analysis circuit 128 is also coupled to controller 126 and can send signals to, and receive signals from, controller 126 so that the two elements can coordinate and optimize operation of device 100. Although the illustrated embodiment shows controller 126 and readout and analysis circuit 128 as physically separate units, in other embodiments the controller and the readout and analysis circuit could be combined in a single unit.

In operation of device 100, the system is first powered up and any necessary logic (i.e., software instructions) is loaded into controller 126 and readout and analysis circuit 128 and initialized. After initialization, the valve in filter and valve unit 104 is opened and pump 112 is set to allow flow through the fluid handling assembly. Fluid is then input to fluid handling assembly 101 through inlet 114 at a certain flow rate and/or for a certain amount of time; the amount of time needed will usually be determined by the time needed for pre-concentrator 106 to generate adequate concentrations of the particular chemicals whose presence and/or concentration are being determined. As fluid is input to the system through inlet 114, it is filtered by filter and valve assembly 104 and flows through elements 104-112 within fluid handling assembly 101 by virtue of the fluid connections between these elements. After flowing through elements 104-112, the fluid exits the fluid handling assembly through exhaust 124.

After the needed amount of fluid has been input through inlet 114, the valve in filter and valve assembly 104 is closed to prevent further input of fluid. After the valve is closed, a heater in pre-concentrator 106 activates to heat the pre-concentrator. The heat releases the chemicals absorbed and concentrated by the pre-concentrator. As the chemicals are released from pre-concentrator 106, pump 112 is activated to draw the released chemicals through gas chromatograph 108 and detector array 110 and output the chemicals through exhaust 124. Activation of pump 112 also prevents backflow through fluid handling assembly 101.

As the chemicals released from pre-concentrator 106 are drawn by pump 112 through gas chromatograph 108, the chromatograph separates different chemicals from each other in the time domain—that is, different chemicals are output from the gas chromatograph at different times. As the different chemicals exit gas chromatograph 108 separated in time, each chemical enters MEMS detection array 110, where sensors in the detection array detect the presence and/or concentration of each chemical. The time-domain separation performed in gas chromatograph 108 substantially enhances the accuracy and sensitivity of MEMS detection array 110, since it prevents numerous chemicals from entering the detection array at the same time and thus prevents cross-contamination and potential interference in the sensors within the array.

As individual sensors within MEMS detection array 110 interact with the entering time-domain-separated chemicals, the detection array senses the interaction and outputs a signal to readout and analysis circuit 128, which can then use the signal to determine presence and/or concentration of the chemicals. When readout and analysis circuit 128 has determined the presence and/or concentration of all the chemicals of interest it can use various analysis techniques, such as correlation and pattern matching, to extract some meaning from the particular combination of chemicals present and their concentrations.

Figure 2:
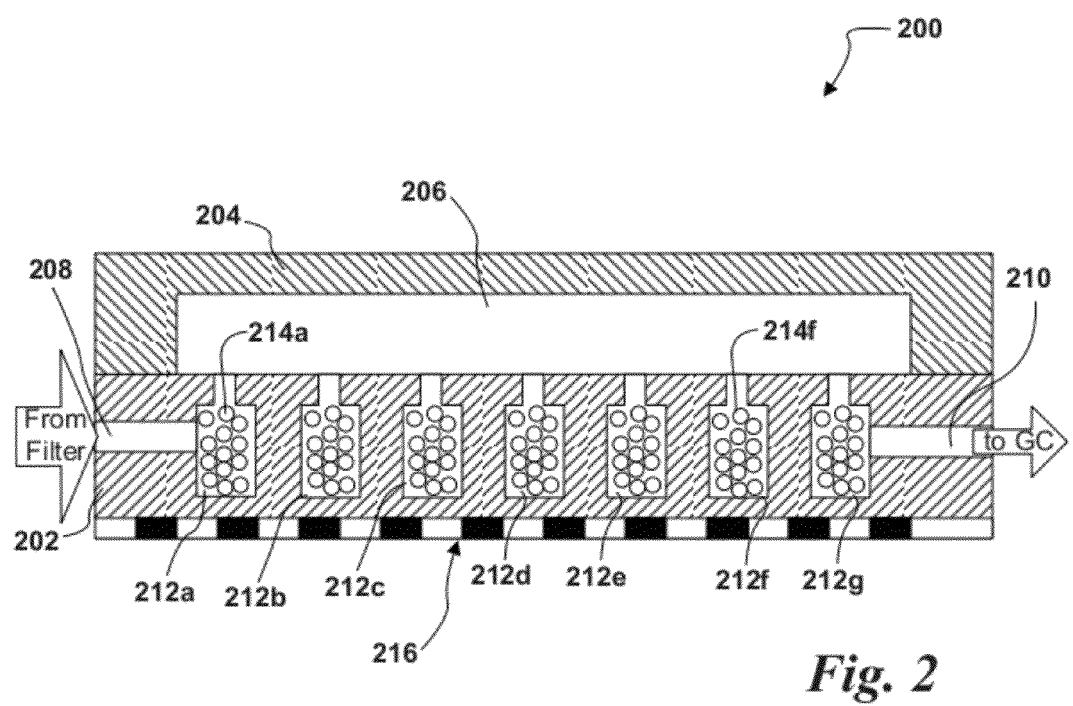
FIG. 2 is a cross-sectional elevation drawing of an embodiment of a MEMS pre-concentrator that can be used in the embodiment of a gas analysis device shown in FIGS. 1A-1B.

FIG. 2 illustrates an embodiment of a MEMS pre-concentrator 200 that can be used as pre-concentrator 106 in device 100. Pre-concentrator 200 includes a substrate 202 having a cover plate 204 bonded thereto and sealed around the perimeter of the substrate to create a cavity 206. Substrate 202 has formed therein an inlet 208 on one side, an outlet 210 on a different side, and pockets 212 having absorbents therein. In one embodiment, substrate 202 is a silicon substrate, but in other embodiments substrate 202 can of course be made of other materials. Heater 216 is formed on the side of substrate 202 opposite the side where cover plate 204 is attached.

In an embodiment where substrate 202 is silicon, inlet 208, outlet 210 and pockets 212 can be formed using standard photolithographic patterning and etching. Although the illustrated embodiment shows seven pockets 212a-212g, the number of pockets needed depends on the number of different chemicals to be absorbed and concentrated, and on the nature of the absorbents used. In an embodiment where each absorbent absorbs only one chemical, the number of pockets 212 can correspond exactly to the number of chemicals to be absorbed and concentrated, but in other embodiments where each absorbent absorbs only one chemical a greater number of pockets can be used to increase the absorption area. In still other embodiments where each absorbent can absorb more than one chemical, a lesser number of pockets can be used.

Each pocket 212 has a corresponding absorbent 214 in its interior—pocket 212a has absorbent 214a, pocket 212b has absorbent 214b, and so on. Although shown in the illustrated embodiment as a granular absorbent, in other embodiments absorbents 214 can be coatings on the walls of pockets 212 or can be a continuous substance that partially or fully fills each pocket 212. Other embodiments can include combinations of granular, wall coatings or continuous filling absorbents. Each absorbent can have a chemical affinity for one or more particular chemicals, meaning that the exact absorbents used will depend on the number and nature of chemicals to be absorbed and concentrated. Examples of absorbents that can be used include cabopack B, cabopack X, etc.

During operation of MEMS pre-concentrator 200 in device 100, fluid from filter and valve assembly 104 enters through inlet 208, passes through absorbent 214a in pocket 212a, and enters cavity 206. Cover plate 204 helps guide fluid entering the cavity 206 into the different pockets 212b-212g and through absorbents 214b-214g, until the fluid, minus the chemicals absorbed by absorbents 214a-214g, exits the pre-concentrator through outlet 210. Once enough fluid has flowed through the pre-concentrator, the valve in filter and valve assembly 104 is closed to prevent further flow through inlet 208. Heater 216 is then activated. Heater 216 heats absorbents 214a-214f, causing them to release the absorbed chemicals through processes such as outgassing. Simultaneously with activating heater 216, or shortly thereafter, pump 112 is activated, drawing the released chemicals out through outlet 210 to gas chromatograph 108.

Figure 3A:
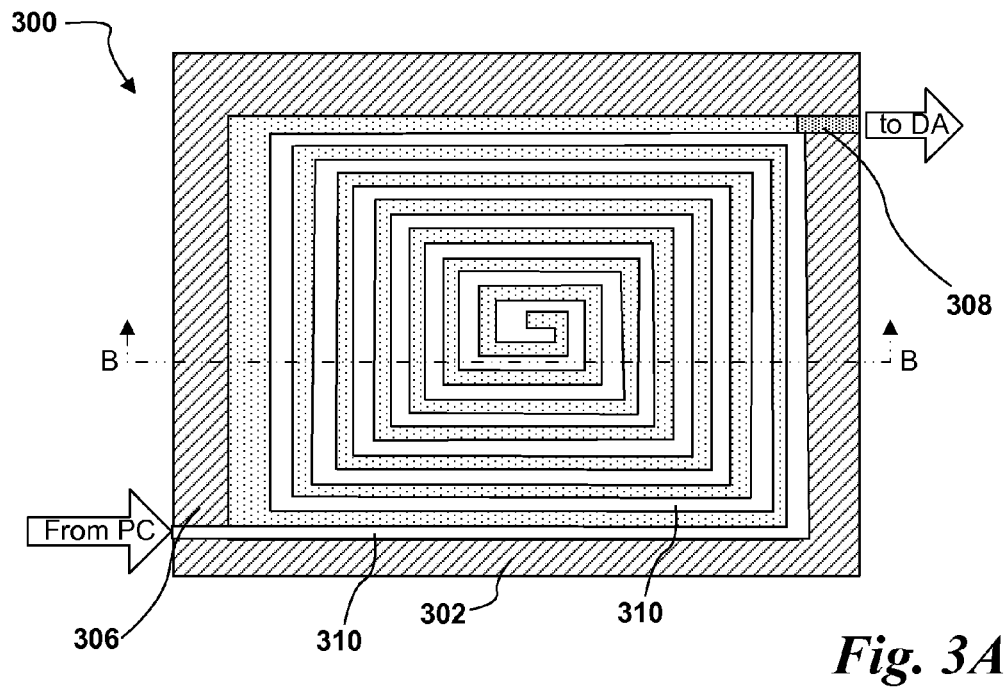
FIG. 3A is a plan view drawing of an embodiment of a MEMS gas chromatograph that can be used in the embodiment of a gas analysis device shown in FIGS. 1A-1B
Figure 3B:
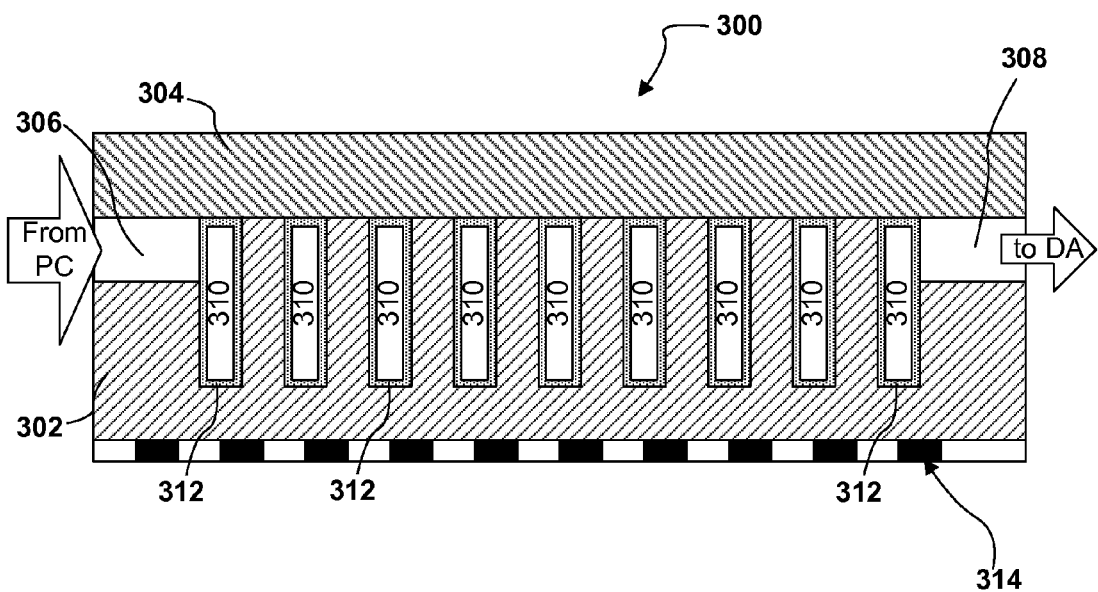
FIG. 3B is a cross-sectional elevation drawing of the embodiment of a MEMS gas chromatograph shown in FIG. 3A, taken substantially along section line B-B.

FIGS. 3A-3B illustrate an embodiment of a MEMS gas chromatograph 300 that can be used as gas chromatograph 108 in device 100. MEMS gas chromatograph 300 includes a substrate 302 with an inlet 306 on one side, an outlet 308 on a different side, and a separation column 310 having a stationary phase coating on its walls. A cover plate 304 is bonded to substrate 302 to seal column 310. In one embodiment substrate 302 is a silicon substrate, but in other embodiments substrate 302 can of course be made of other materials. In an embodiment where substrate 302 is silicon, inlet 306, outlet 308 and column 310 can be formed using standard photolithographic patterning and etching, such as deep reactive ion etching (DRIE). Heater 314 is formed on the side of substrate 302 opposite the side where cover plate 204 is attached.

Column 310 provides a continuous fluid path from inlet 306 to outlet 308, and some or all of the walls of column 310 are coated with a stationary phase coating that can interact with the chemicals being separated by the chromatograph. How thoroughly and how fast chemicals are separated from the fluid depend on the stationary phase coating, the overall path length of column 310, and the temperature. For a given stationary phase coating, the longer the column the better the chemical spectrum separation, but a long column also extends the separation time. For a given application, the required path length will therefore usually be determined by a tradeoff among the coating, the column length and the temperature. The illustrated embodiment shows column 310 as a spiral column in which the column path length will depend on the number of coils in the spiral. In other embodiments, however, column 310 can be shaped differently.

During operation of MEMS gas chromatograph 300 in device 100, fluid from pre-concentrator 106 enters through inlet 306 and passes through column 310. As fluid passes through the column 310, the different chemicals in the fluid interact with stationary phase coating 312 at different rates, meaning that the chemicals are separated after traveling through the column, with the chemicals that interact strongly with the stationary phase being separated first and the chemicals that interact weakly with the stationary phase being separated last. In other words, chemicals that interact strongly with the stationary phase are retained longer in the stationary phase, while chemicals that interacted weakly with the stationary phase retained less time in the stationary phase. In some embodiments of gas chromatograph 300 this time-domain separation can occur according to molecular weight (e.g., chemicals with the lowest molecular weight are separated first, followed by higher molecular weights), but in other embodiments it can occur according to other chemical characteristics or other separation mechanisms. As the chemicals are time-domain separated, pump 112 draws them out of MEMS gas chromatograph 300 through outlet 308. Generally, the chemicals exit through outlet 308 in the reverse order of their separation—that is, chemicals with low retention time exit first, while chemicals with higher retention times exit later. After leaving outlet 308, the chemicals enter detector array 110.

Figure 4A:
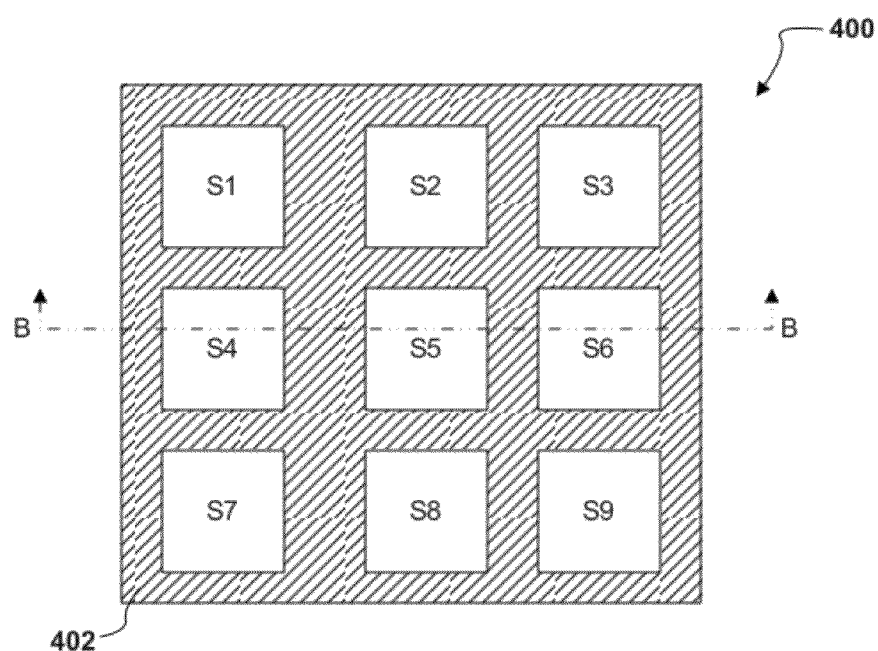
FIG. 4A is a plan view drawing of an embodiment of a detector array that can be used in the embodiment of a gas analysis device of FIGS. 1A-1B.
Figure 4B:
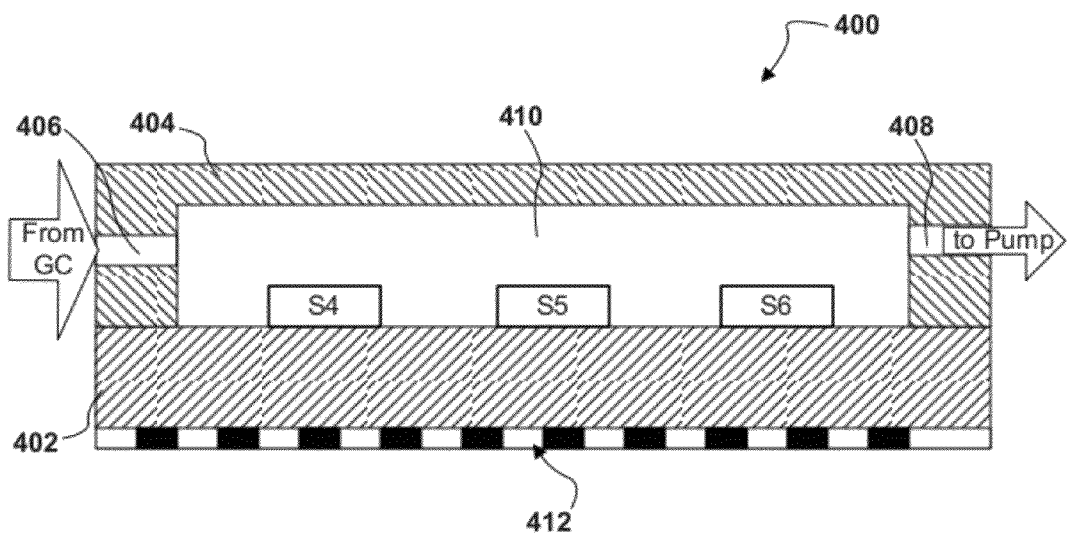
FIG. 4B is a cross-sectional elevation drawing of the embodiment of a detector array shown in FIG. 4A, taken substantially along section line B-B.

FIGS. 4A-4B illustrate an embodiment of a detector array 400 that can be used as detector array 110 in device 100. Detector array 400 includes a substrate 402 with an array of sensors S1-S9 formed thereon. In the illustrated embodiment sensors S1-S9 form a regularly shaped 3-by-3 array of sensors, but in other embodiments the sensor array can have a greater or lesser number of sensors, and the sensors can be arranged in any pattern, regular or irregular.

A cover 404 is bonded to the perimeter of substrate 402 to form a cavity 410 within which sensors S1-S9 are located. Cover 404 also includes an inlet 406 through which fluid can enter from gas chromatograph 108 and an outlet 408 through which fluid can exit to pump 112. A heater 412 is formed on the side of substrate 402 opposite the side where cover 404 is attached to control the temperature of detector array 400, and hence the sensors within the detector array, during operation. Although not shown in the figure, detector array 400 of course includes outputs by which signals generated by sensors S1-S9 can be output for processing.

Each sensor S1-S9 includes a surface with a coating thereon. Each coating used will have an affinity for one or more of the particular chemicals being detected, such that the coating absorbs or chemically interacts with its corresponding chemical or chemicals. The interaction between coating and chemical in turn changes a physical property of the sensor such as resonant frequency, capacitance or electrical resistance, and that changed physical property of the sensor can be measured using a transducer or other measurement device. The particular coatings chosen for sensors S1-S9 will depend on the chemicals that sensor array 110 will be used to detect. The chemical affinity of coatings also varies strongly with temperature, so that the operating temperature range should be considered in selecting coatings. In an embodiment where sensor array 110 will be used to detect volatile organic compounds in human breath—such as benzene, toluene, n-octane, ethylbenzene, m,p-xylene, α-pinene, d-limonene, nonanal, and benzaldehyde, 2-methylhexane, 4-methyloctane, and so on—coatings that can be used in different applications include amorphous copolymers of 2,2-bistrifluoromethyl-4,5-difluoro-1,3-dioxole (PDD) and tetrafluoroethylene (TFE), $PtC12$ (olefin), C8-MPN, etc.

Although the illustrated embodiment has nine sensors, the number of sensors needed depends on the number of different chemicals to be detected, and on the nature of the coatings used on the sensors. In an embodiment where each coating absorbs or chemically interacts with only one chemical the number of sensors can correspond exactly to the number of chemicals to be detected, but in other embodiments it can be desirable to have a given coating on more than one sensor for redundancy. In most cases, however, there is no one-to-one correlation between chemicals to coatings; in other words, each coating reacts with more than one different chemical and the reaction between different chemicals and a given coating will vary in nature and strength. A detector array having sensors with different coatings is therefore useful because the response of the detector array can have different patterns for different gases.

In one embodiment of sensor array 400, sensors S1-S9 are MEMS sensors positioned on the surface of substrate 402, meaning that they are surface micromachined sensors. In other embodiments using MEMS sensors, however, sensors S1-S9 can be bulk micromachined sensors, meaning that at least some of the MEMS sensors are formed within substrate 402 instead of on the surface. Still other embodiments of sensor array 110 using MEMS sensors can include combinations of surface-micromachined and bulk-micromachined sensors.

Different types of MEMS sensors can be used, depending on the application and the required sensitivity. Examples of MEMS sensors that can be used include chemiresistors, bulk acoustic wave (BAW) sensors, etc. In other embodiments of detector array 400, one or more of sensors S1-S9 can be a non-MEMS sensor. Examples of non-MEMS sensors that can be used in detector array 400 include SAW (surface acoustic wave) sensors with quartz or Gallium Arsenide (GaAs) substrates.

During operation of MEMS detector array 400 in device 100, fluid from gas chromatograph 108 enters through inlet 406 and passes into cavity 410. Fluid entering cavity 410 carries time-domain separated chemicals. As each chemical enters cavity 410 it interacts with one or more sensors whose coating has an affinity for that chemical. The interaction of the chemical with the sensor is sensed and measured, and the presence and concentration of the particular chemical can be extracted. As more fluid flows into cavity 410, the first chemical is pushed out of cavity 410 through outlet 408 and fluid with the next time-domain-separated chemical enters cavity 410, interacts with the sensor array and is measured. This process continues until all the time-domain-separated chemicals from gas chromatograph 108 have flowed through detector array 110. In some embodiments where the affinity of the coatings for their chemicals is not strong, detector array 110 can be re-usable: after all time-domain-separated chemicals have been sensed, heater 412 can be activated to heat the sensors and cause the coatings to release the respective chemicals with which they interacted, making the interaction reversible. In embodiments where the affinity of each coating for its chemicals could be strong, heating of the sensor array could help release the partially absorbed gas from the coating materials.

Figure 5:
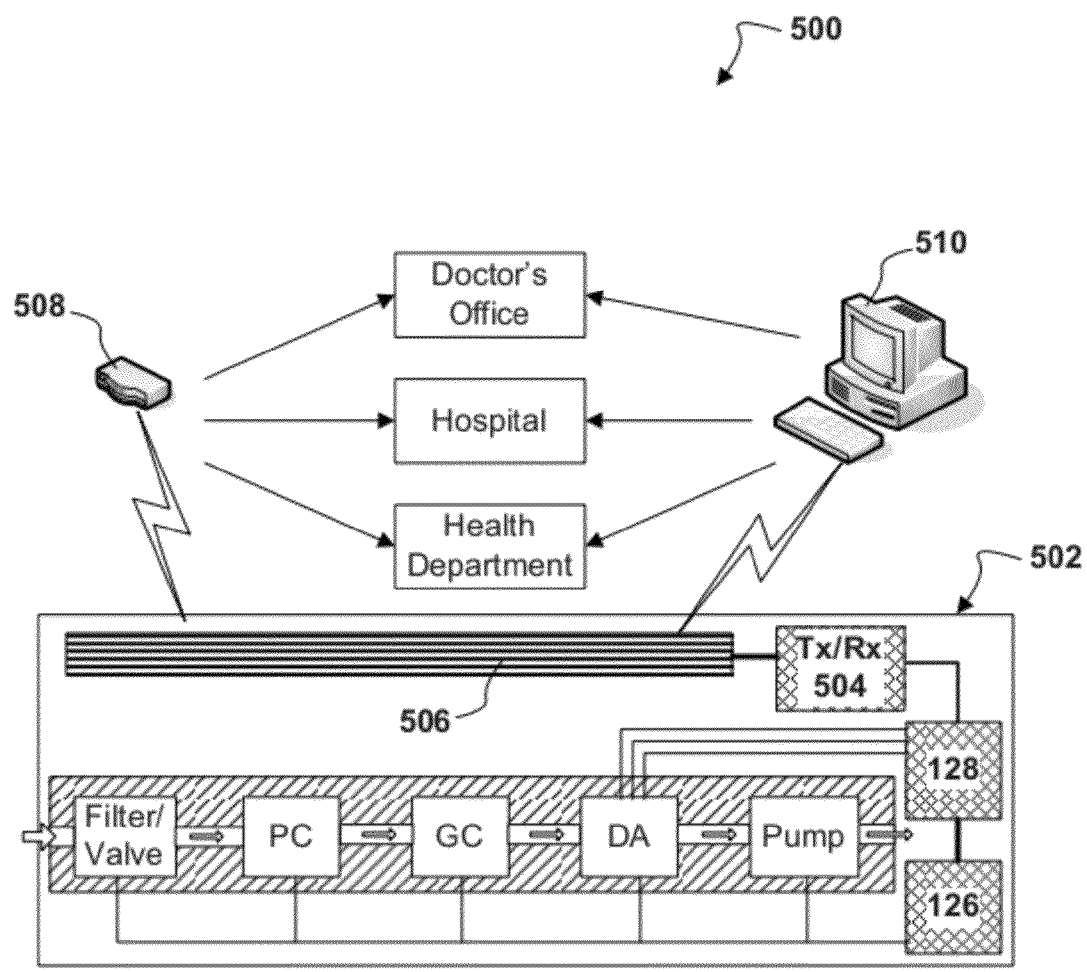
FIG. 5 is a schematic diagram of an alternative embodiment of a gas analysis device and an embodiment of a system using the embodiment of the gas analysis device.

FIG. 5 illustrates an embodiment of a system 500 using an alternative embodiment of a MEMS-based gas analysis device 502. Device 502 is in most respects similar to device 100. The primary difference between device 502 and device 100 is the presence in device 502 of a wireless transceiver circuit 504 and an antenna 506 mounted on substrate 102. Wireless transceiver circuit 504 can both transmit (Tx) data and receive (Rx) data and is coupled to reading and analysis circuit 128 and antenna 506.

In one embodiment of system 500, transceiver 504 can be used to wirelessly transmit raw data from reading and analysis circuit 128 to one or both of a router 508 and a computer 510. When transmitted to router 508, the data can then be re-transmitted to another destination for analysis. For example, in an application where device 502 is used for health-related chemical analysis, data sent to router 508 can be re-transmitted to one or more of a doctor's office, a hospital, a government health department, or someplace else for analysis and interpretation. After analysis is complete, or if there is a problem with the data, the doctor's office, hospital or health department can send instructions to device 502 through router 508, antenna 506 and transceiver 504 to signal the result, to try to fix or improve the data, or to signal that the test must be performed again.

Continuing with the same health-care example, in the same or another embodiment of system 500, wireless transceiver 504 can be used to transmit raw data to computer 510. Computer 510 can either forward the raw data to a doctor, hospital, etc., as did the router, or can analyze the data with software installed thereon to provide extract information from the data, such as one or more possible medical diagnoses, and provide the extracted information to the user of device 502. When it provides analysis and medical diagnoses, computer 510 can also forward the diagnosis, alone or with the analysis and raw data, on to the doctor, hospital, etc. As with the router, the doctor's office, hospital or health department can send instructions to device 502 through computer 510, antenna 506 and transceiver 504 to try to fix or improve the data, to signal that the test must be performed again, and so on.

Again continuing with the same health-care example, in still another embodiment of system 500 the raw data can be processed, and information such as potential diagnoses extracted from the data, by reading and analysis circuit 128. The potential diagnoses determined by reading and analysis circuit 128 can then be sent to computer 510 to be reviewed by the user and/or forwarded, or can be immediately forwarded alone or with the supporting raw data to the doctor's office, etc.

Figure 6:
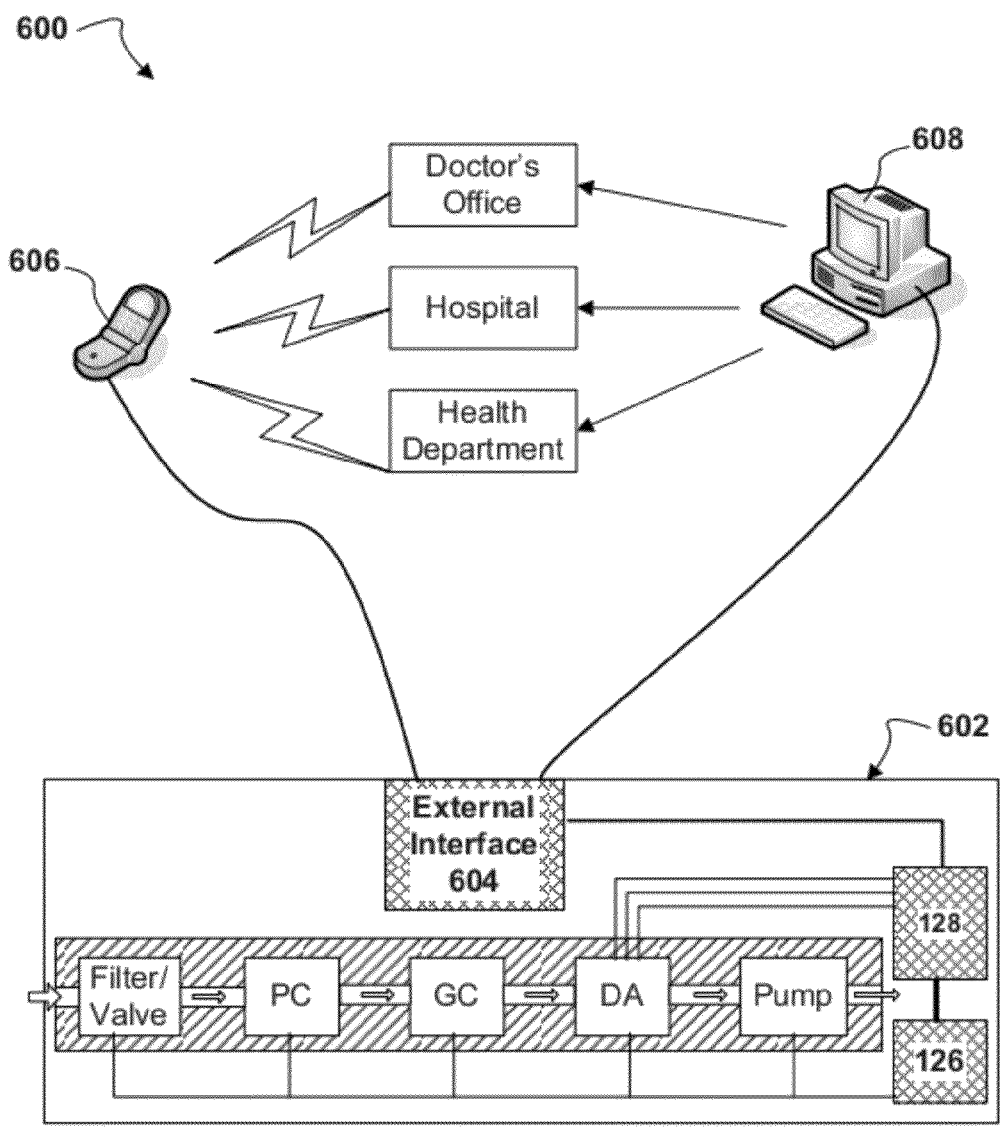
FIG. 6 is a schematic diagram of another alternative embodiment of a gas analysis device and an embodiment of a system using the embodiment of the gas analysis device.

FIG. 6 illustrates an embodiment of a system 600 using an alternative embodiment of a MEMS-based gas analysis device 602. Device 602 is in most respects similar to device 502. The primary difference between device 602 and device 502 is that the wireless transceiver circuit 504 and antenna 506 are replaced with a hardware data interface 604 coupled to reading and analysis circuit 128. In one embodiment, hardware data interface 604 could be a network interface card, but in other embodiments hardware data interface can be an Ethernet card, a simple cable plug, etc. External devices can be connected to device 602 through traditional means such as cables. Although it has a different communication interface, device 602 and system 600 have all the same functionality as device 502 and system 500. As with system 500, in system 600 MEMS-based gas analysis device 602 can transmit data to, and receive data from, one or both of a computer 608 and a wireless device 606, such as a cell phone or personal digital assistant (PDA). When transmitted to wireless device 606 the data can then be forwarded to a doctor's office, hospital, or government health department, and the recipients of the data can in turn send data or instructions back to gas analysis device 602 through the wireless device. As in system 500, when data is transmitted to computer 608 it can be forwarded or can be analyzed by the computer and the result displayed for the user and/or forwarded, and instructions can be transmitted to device 602 through computer 608. Similarly, the data from gas analysis device 602 can be analyzed by reading and analysis circuit 128. After analysis by circuit 128, the extracted information (e.g., one or more diagnoses) and/or the raw data can be forwarded via the hardware data interface 604.

Figure 7:
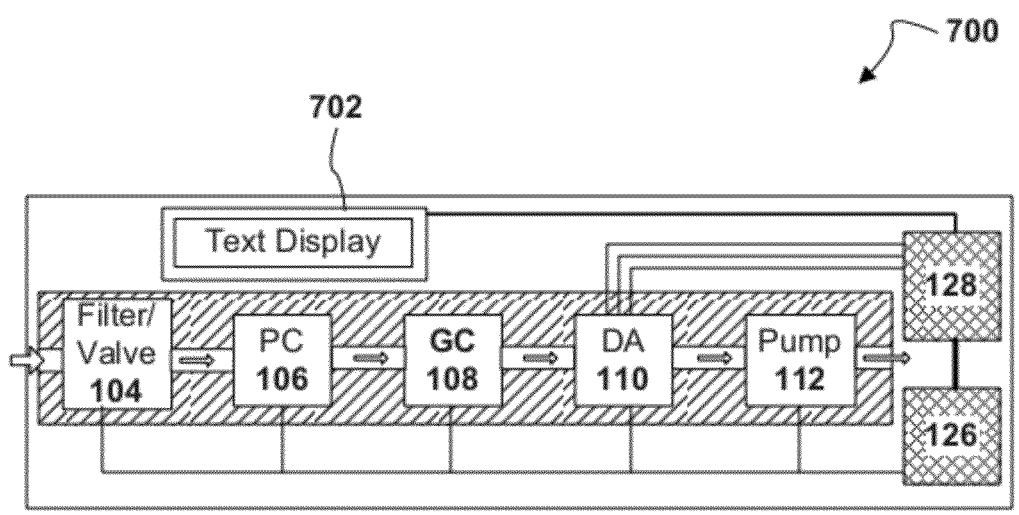
FIG. 7 is a plan-view schematic diagram of an additional alternative embodiment of a gas analysis device.

FIG. 7 illustrates an alternative embodiment of a MEMS-based gas analysis device 700. Device 700 is in most respects similar to device 100. The primary difference between system 700 and device 100 is that device 700 includes an on-board display 702 for conveying to a user the results of the analysis performed by reading and analysis circuit 128.

The illustrated embodiment uses an on-board text display 702, for example an LCD screen that can convey text information to a user. For example, in a health care example display 702 could be used to display the test results in analog numbers indicating the situation of patients. Display 702 could indicate a positive or negative diagnosis, could indicate probabilities of a given diagnosis, or could indicate the raw data from the detector array. In another health care embodiment, simpler displays can be used, such as one with three lights that indicate a positive, negative, or indeterminate result depending on which light is switched on.

Figure 8:
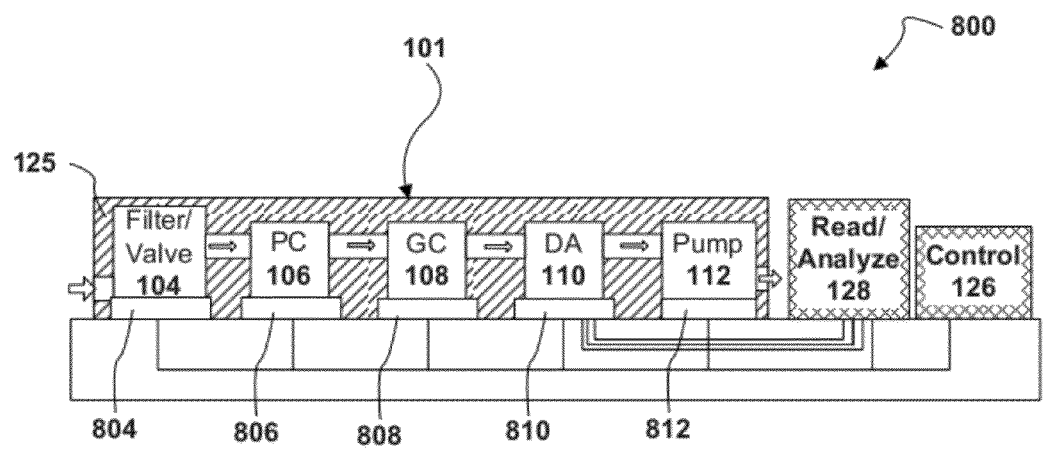
FIG. 8 is a plan-view schematic diagram of an additional alternative embodiment of a gas analysis device.

FIG. 8 illustrates an alternative embodiment of a MEMS-based gas analysis device 800. Device 800 is in most respects similar to device 100. The primary difference between device 800 and device 100 is that in device 800 one or more elements of fluid handling assembly 101 are replaceable. In the illustrated embodiment, the elements are made replaceable by mounting them onto substrate 102 using sockets: filter and valve assembly 104 is mounted to substrate 102 by socket 804, pre-concentrator is mounted to substrate 102 by socket 804, gas chromatograph 108 is mounted to substrate 102 by socket 808, detector array 110 is mounted to substrate 102 by socket 810, and pump 112 is mounted to substrate 102 by socket 812. In one embodiment, sockets 804-812 are sockets such as zero insertion force (ZIF) sockets that permit easy replacement by a user, but in other embodiments other types of sockets can be used. Although the illustrated embodiment shows all the components of fluid handling assembly 101 being replaceable, in other embodiments only some of the components such as pump 112 and detector array 110 can be made replaceable.

Figure 9:
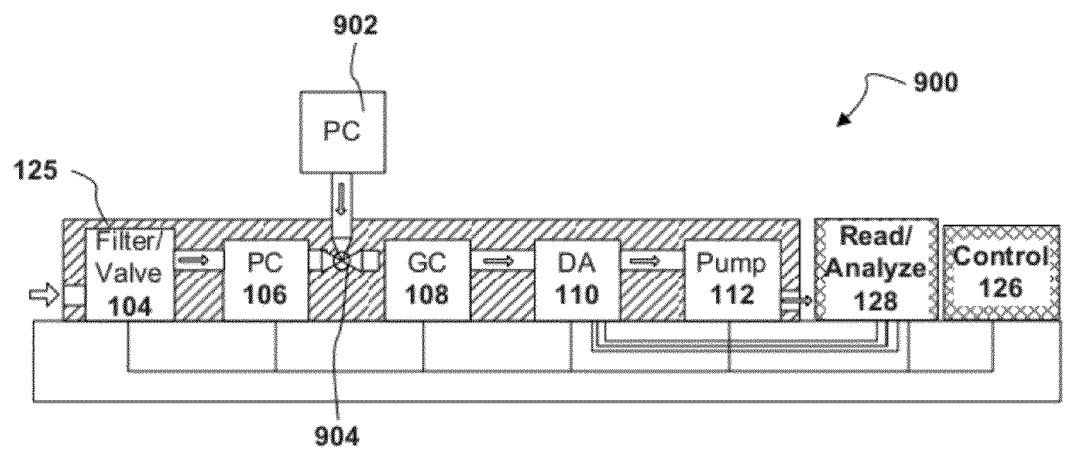
FIG. 9 is a plan-view schematic diagram of an additional alternative embodiment of a gas analysis device.

FIG. 9 illustrates an alternative embodiment of a MEMS-based gas analysis device 900. Gas analysis device 900 is in most respects similar to device 100. The primary difference between device 900 and device 100 is that device 900 includes provisions for an external pre-concentrator 902 (i.e., a pre-concentrator not mounted on substrate 102). In the embodiment shown, a valve 904 is placed between pre-concentrator 106 and gas chromatograph 108, and provisions are made to attach external pre-concentrator 902 to the valve. Valve 904 allows the user to use external pre-concentrator 902 instead of, or in addition to, on-board pre-concentrator 106. In one embodiment external pre-concentrator 902 is a breath collection bag, but in other embodiments it can be something different. In an alternative embodiment of device 900 (not shown), pre-concentrator 106 can be permanently removed and replaced by external pre-concentrator 902. In another embodiment where external pre-concentrator 902 replaces pre-concentrator 106, instead of inserting a valve between pre-concentrator 106 and gas chromatograph 108, external pre-concentrator 902 can be coupled upstream of the filter and valve assembly 104.

Device Applications

Pre-clinical studies on human breath analysis have found that certain volatile organic compounds (VOCs) of exhaled human breath are correlated to certain diseases, such as pneumonia, pulmonary tuberculosis (TB), asthma, lung cancer, liver diseases, kidney diseases, etc. The correlations are especially evidential for lung-related diseases. Current analytical systems still rely on large and expensive laboratory instruments, such as gas chromatography (GC) and mass spectrometry (MS). Mass spectrometers in particular are impossible to miniaturize, making widespread use of these diagnostic instruments impossible.

The embodiments of MEMS-based gas analysis sensors discussed above provide a solution to this problem, and in particular could be used advantageously to diagnose and monitor various diseases such as asthma, lung cancer, lung-related diseases, and other non-lung diseases such as kidney and liver diseases, and etc.

Asthma

Asthma is a chronic disease; therefore, regularly monitoring patient's status is helpful to doctor on tracking patient's healing progresses. Therefore, the new idea of handheld diagnostics would make the breath analysis possible done at home or anywhere. In current diagnostics the basic measurement is peak flow rate and the following diagnostic criteria are used by the British Thoracic Society, but the peak flow rate is a physical quantity measurement. Breath analysis could provide specific root causes of the bronchi contraction by measuring the VOCs from patient's breath. Embodiments of the MEMS-based gas analysis systems could be used to monitor the efficacy of the medication. Furthermore, the medication therapy can be tailored to individual patient through this active monitoring by using this home-based device.

Tuberculosis

One third of the world's current population has been infected by TB. And 75% of the cases are pulmonary TB. The infected rate in the developing countries is much higher than developed countries. Therefore, there are urgent needs of developing affordable diagnostic devices for developing countries. Embodiments of the MEMS-based gas analysis system would provide a cost-effective solution. Tuberculosis is caused by Mycobacterium. Current diagnostic is time consuming and difficult since culturing the slow growing Mycobacterium takes about 6 weeks. Therefore, a complete medical evaluation, including chest X-ray, Tuberculosis radiology, tuberculin skin test, microbiological smears and cultures, is used to get more accurate assessment. Therefore, the rapid diagnostic is very valuable and our breath analysis approach could achieve such needs.

Lung Cancer

With early detection and treatment, the 5-year survival rate for lung cancer improves dramatically. Current diagnostic methods, such as chest X-ray and CT (computed tomography) scan, are difficult to detect early stage lung cancer. Breath analysis using embodiments of the MEMS-based gas analysis system could diagnose the early stage lung cancer.

Classification of Lung-Related Diseases with Similar Symptoms

Breath analysis on exhaled VOCs is viable method to identify patient's lung-related diseases, which has similar symptoms. For example, embodiments of the MEMS-based gas analysis system can provide the tested data to medical doctors to classify which disease between cool, lung-cancer, or pneumonia the patient would have. Breath analysis would be the first screening test because of its simplicity before going for more tedious diagnostic measurements.

The above description of illustrated embodiments of the invention, including what is described in the abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. These modifications can be made to the invention in light of the above detailed description.

The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

The invention claimed is:

1. An apparatus comprising:
    a substrate;
    a fluid-handling assembly coupled to the substrate, the fluid-handling assembly including a plurality of fluid-handling components removably coupled to the substrate and removably coupled to each other, the plurality of fluid handling components including:
        a gas chromatograph having a fluid inlet and a fluid outlet, and
        a detector array having a fluid inlet and a fluid outlet, wherein the fluid inlet of the detector array is fluidly coupled to the fluid outlet of the gas chromatograph;
    a shroud covering the plurality of fluid-handling components;
    a control circuit communicatively coupled to at least one of the plurality of fluid-handling components; and
    a readout circuit communicatively coupled to the detector array and to the control circuit.

2. The apparatus of claim 1 wherein the readout circuit includes an analysis circuit and associated logic to analyze an output signal received from the detector array.

3. The apparatus of claim 2, further comprising an indicator coupled to an output of the analysis circuit to indicate to a user a result of the analysis.

4. The apparatus of claim 1 wherein the plurality of fluid-handling components further comprises a pre-concentrator having a fluid inlet and a fluid outlet, wherein the pre-concentrator is removably coupled to the control circuit and wherein the fluid outlet of the pre-concentrator is removably coupled to the fluid inlet of the gas chromatograph.

5. The apparatus of claim 4 wherein the plurality of fluid-handling components further comprises a filter and valve unit having a fluid inlet and a fluid outlet, wherein the filter and valve unit is removably coupled to the control circuit and wherein the fluid outlet of the filter and valve unit is removably coupled to the fluid inlet of the pre-concentrator.

6. The apparatus of claim 5 wherein the plurality of fluid-handling components further comprises a pump having a fluid inlet and a fluid outlet, wherein the pump is removably coupled to the control circuit and wherein the fluid inlet of the pump is removably coupled to the fluid outlet of the detector array.

7. The apparatus of claim 5 wherein fluid couplings provide the removable couplings among the plurality of fluid-handling components.

8. The apparatus of claim 1 wherein the shroud provides the removable couplings among the plurality of fluid-handling components.

9. The apparatus of claim 1 wherein the substrate is a printed circuit board that includes electrical connections that communicatively couple the control circuit to one or more of the plurality of fluid-handling components and the readout circuit to the detector array.

10. The apparatus of claim 1 wherein the detector array includes one or more MEMS detectors, wherein at least one of the one or more MEMS detectors can be a chemiresistor or a bulk acoustic wave sensor.

11. The apparatus of claim 1 wherein the detector array includes one or more non-MEMS detectors, wherein at least one of the one or more non-MEMS detectors can be a surface acoustic wave sensor.

12. A system comprising:
a gas analysis device comprising:
  a substrate;
  a fluid-handling assembly coupled to the substrate, the fluid-handling assembly including a plurality of fluid-handling components removably coupled to the substrate and removably coupled to each other, the plurality of fluid handling components including:
    a gas chromatograph having a fluid inlet and a fluid outlet, and
    a detector array having a fluid inlet and a fluid outlet, wherein the fluid inlet of the detector array is fluidly coupled to the fluid outlet of the gas chromatograph;
  a shroud covering the plurality of fluid-handling components;
  a control circuit communicatively coupled to at least one of the plurality of fluid-handling components;
  a readout circuit communicatively coupled to the detector array and to the control circuit; and
  a communication interface coupled to the readout circuit.

13. The system of claim 12, further comprising a pre-concentrator having a fluid inlet and a fluid outlet, wherein the pre-concentrator is removably coupled to the control circuit and wherein the fluid outlet of the pre-concentrator is removably coupled to the fluid inlet of the gas chromatograph.

14. The system of claim 13, further comprising a filter and valve unit having a fluid inlet and a fluid outlet, wherein the filter and valve unit is removably coupled to the control circuit and wherein the fluid outlet of the filter and valve unit is removably coupled to the fluid inlet of the pre-concentrator.

15. The system of claim 14, further comprising a pump having a fluid inlet and a fluid outlet, wherein the pump is removably coupled to the control circuit and wherein the fluid inlet of the pump is removably coupled to the fluid outlet of the detector array.

16. The system of claim 12 wherein the readout circuit includes an analysis circuit and associated logic to analyze the output signals received from the detector array.

17. The system of claim 12 wherein the communication interface comprises a wireless transceiver mounted on the substrate and an antenna mounted to the substrate and coupled to the wireless transceiver.

18. The system of claim 17, further comprising one or both of a router and a computer with which the gas analysis device can communicate through the wireless transceiver and the antenna.

19. The system of claim 12 wherein the communication interface comprises a hardware data interface.

20. The system of claim 19, further comprising one or both of a wireless device and a computer with which the gas analysis device can communicate through the hardware data interface.

21. An apparatus comprising:
a substrate;
a fluid-handling assembly coupled to the substrate, the fluid-handling assembly including a plurality of fluid-handling components removably coupled to the substrate and removably coupled to each other, the plurality of fluid handling components including:
  a gas chromatograph having a fluid inlet and a fluid outlet,
  a pre-concentrator having a fluid inlet and a fluid outlet, wherein the fluid outlet of the pre-concentrator is coupled to the fluid inlet of the gas chromatograph, and
  a detector array having a fluid inlet and a fluid outlet, wherein the fluid inlet of the detector array is fluidly coupled to the fluid outlet of the gas chromatograph;
a shroud covering the plurality of fluid-handling components;
an external pre-concentrator having a fluid inlet and a fluid outlet coupled to the fluid coupling between the outlet of the pre-concentrator and the inlet of the gas chromatograph;
a control circuit communicatively coupled to at least one of the plurality of fluid-handling components; and
a readout circuit communicatively coupled to the detector array and to the control circuit.

22. The apparatus of claim 21, further comprising a three-way valve removably coupled to the fluid outlet of the pre-concentrator, to the fluid inlet of the gas chromatograph, and to the fluid outlet of the external pre-concentrator.

23. The apparatus of claim 21 wherein the readout circuit includes thereon an analysis circuit and associated logic to analyze an output signal received from the detector array.

24. The apparatus of claim 21 wherein the plurality of fluid-handling components further comprises a filter and valve unit having a fluid inlet and a fluid outlet, wherein the filter and valve unit is removably coupled to the control circuit and wherein the fluid outlet of the filter and valve unit is removably coupled to the fluid inlet of the pre-concentrator.

25. The apparatus of claim 24 wherein the plurality of fluid-handling components further comprises a pump having a fluid inlet and a fluid outlet, wherein the pump is removably coupled to the control circuit and wherein the fluid inlet of the pump is removably coupled to the fluid outlet of the detector array.

26. The apparatus of claim 21 wherein the shroud provides the removable coupling among the plurality of fluid-handling components.

27. The apparatus of claim 21 wherein fluid couplings provide the removable coupling among the plurality of fluid-handling components.

28. The apparatus of claim 21 wherein the substrate is a printed circuit board that includes electrical connections that communicatively couple the control circuit to one or more of the plurality of fluid-handling components and the readout circuit to the detector array.

* * * * *